(12) United States Patent
O'Toole et al.

(10) Patent No.: US 7,300,647 B1
(45) Date of Patent: *Nov. 27, 2007

(54) HAIR CARE COMPOSITIONS

(75) Inventors: Edel Bernadette O'Toole, Staines (GB); Stephen Robert Schofield, Bracknell (GB); Paul Meredith, Woking (GB); Christopher Lawrence Gummer, Chilworth (GB)

(73) Assignee: The Procter & Gamble Company, Cincinnati, OH (US)

( * ) Notice: Subject to any disclaimer, the term of this patent is extended or adjusted under 35 U.S.C. 154(b) by 784 days.

This patent is subject to a terminal disclaimer.

(21) Appl. No.: 10/049,497

(22) PCT Filed: Feb. 24, 2000

(86) PCT No.: PCT/US00/04709

§ 371 (c)(1),
(2), (4) Date: Feb. 13, 2002

(87) PCT Pub. No.: WO00/51545

PCT Pub. Date: Sep. 8, 2000

(30) Foreign Application Priority Data

Jun. 14, 1999 (GB) ................................ 9913764.8

(51) Int. Cl.
*A61K 8/00* (2006.01)
*A61K 38/00* (2006.01)
*A61K 8/02* (2006.01)

(52) U.S. Cl. .................... 424/70.1; 424/401; 514/2
(58) Field of Classification Search .............. 424/401, 424/701, 400; 514/2
See application file for complete search history.

(56) References Cited

U.S. PATENT DOCUMENTS

| 4,201,235 A | | 5/1980 | Ciavatta |
| 4,419,343 A | * | 12/1983 | Pauly ........................ 424/59 |
| 4,620,850 A | | 11/1986 | Bachmann et al. |
| 5,053,230 A | * | 10/1991 | Gazzani ..................... 424/582 |
| 5,290,562 A | * | 3/1994 | Meybeck et al. ........... 424/450 |
| 5,458,881 A | | 10/1995 | Berger |
| 6,129,770 A | | 10/2000 | Deutz et al. |
| 6,544,500 B1 | * | 4/2003 | O'Toole et al. ............ 424/70.1 |

FOREIGN PATENT DOCUMENTS

| DE | 1617477 | 1/1970 |
| DE | 4225693 A1 | 2/1994 |
| EP | 0435012 B1 | 4/1994 |
| EP | 0181773 B2 | 1/1999 |
| JP | 57-109711 A | 7/1982 |
| JP | 59-078114 A | 5/1984 |
| JP | 01-216908 A | 8/1989 |
| JP | 04-103517 A | 4/1992 |
| JP | 00-191457 A | 7/2000 |
| WO | WO-96/17586 A1 | 6/1996 |
| WO | WO-97/35542 A1 | 10/1997 |
| WO | WO-97/35545 A1 | 10/1997 |
| WO | WO-97/35546 A1 | 10/1997 |
| WO | WO-00/51552 A2 | 9/2000 |

* cited by examiner

*Primary Examiner*—Lakshmi S. Channavajjala
(74) *Attorney, Agent, or Firm*—Idris N. McKelvey; Marianne Dressman

(57) ABSTRACT

According to the present invention there is provided a hair care composition comprising at least one tyrosine compound and at least one other amino acid compound selected from tryptophan compounds, histidine compounds and lysine compounds. The compositions of the present invention can improve the strength and condition of the hair.

7 Claims, No Drawings

HAIR CARE COMPOSITIONS

The present invention relates to hair care compositions. In particular, it relates to hair care compositions comprising certain amino acid compounds.

BACKGROUND TO THE INVENTION

Hair is often subjected to a wide variety of insults that can cause weakening and damage. These include shampooing, rinsing, drying, heating, combing, styling, perming, colouring, exposure to the elements etc. Thus the hair is often in a dry, rough, lusterless or frizzy condition due to abrasion of the hair surface and removal of the hair's natural oils and other natural conditioning and moisturizing components.

A variety of approaches have been developed to alleviate these conditions. These include the use of ultra mild shampoo compositions, the use of hair conditioning shampoos which attempt to both cleanse and condition the hair from a single product and the use of hair conditioning formulations such as rinse-off, leave-on or heat activated products. See, for example, EP-A-181,773, WO-A-97/35542, WO-A-97/35545, WO-A-97/35546, all of which describe conditioning shampoo compositions.

It has been suggested that amino acids may be used in hair care compositions for providing a variety of benefits. For example, U.S. Pat. No. 4,201,235 describes compositions comprising various amino acids that enhance the luster and softness of the hair. JP-A-57/109711 describes compositions comprising amino acids which improve the combing properties of the hair. DE-A-1,617,477 describes hair tonic with guaranteed hair growth comprising certain amino acids. JP-A-59/078114 describes compositions for imparting a smooth feeling to the hair containing amine oxide compounds and amino acids having an isoelectric point of 7 or lower.

It has been found that the levels of certain amino acids are reduced in damaged hair in comparison with undamaged hair. In particular, it has been found that cysteine, tyrosine, lysine, histidine, methionine and tryptophan are at reduced levels in damaged hair. Surprisingly, it has been found that compositions comprising a tyrosine compound and at least one other amino acid compound selected from tryptophan compounds, histidine compounds and lysine compounds can improve the strength and condition of the hair.

SUMMARY OF THE INVENTION

According to the present invention there is provided a hair care composition comprising at least one tyrosine compound and at least one other amino acid compound selected from tryptophan compounds, histidine compounds and lysine compounds.

The compositions of the present invention can improve the strength and condition of the hair.

All percentages herein are by weight of the composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials which may be combined with the ingredient in commercially available products.

All documents referred to herein, including all patents, all patent applications and all articles, are hereby incorporated herein by reference in their entirety unless otherwise indicated.

The term "alkyl" as used herein, unless otherwise indicated, means carbon containing moiety which may be straight, branched or cyclic; saturated or unsaturated; unsubstituted or substituted. As used herein "cyclic alkyl" means a carbon containing moiety where all or a portion of the total number of carbon atoms are comprised in a ring structure. Cyclic alkyl includes monocyclo bicyclo- and tricyclo-alkyl. Cyclic alkyl includes carbon-containing ring structures that comprise one or more heteroatoms. Preferred are cyclic alkyl with one or two heteroatoms.

As used herein "heteroatom" means a nitrogen, sulphur or oxygen atom, preferably nitrogen.

Preferred alkyl are as noted in this paragraph unless otherwise provided in specific instances. Preferred alkyl are saturated and unsubstituted. Preferred alkyl substituents are selected from halo, amino, hydroxy, alkoxy, nitro, thio, oxo, and trifluoromethyl, especially amino. As used herein "alkoxy" is —O-alkyl. It is preferred that substituted alkyl be mono di- or tri-substituted, especially mono-substituted. Preferred alkyl have from 1 to 12 carbon atoms, more preferably 1 to 8, even more preferably 1 to 4.

The term "aryl" as used herein, unless otherwise indicated, means carbon containing ring structures which have delocalised electrons. Aryl includes ring structures that comprise one or more heteroatoms. The preferred heteroatom is nitrogen. If present, it is preferred that there are one or two heteroatoms.

Preferred aryl are as noted in this paragraph unless otherwise provided in specific instances. Preferred aryl are mono bi- or tricyclic, especially mono- and bicyclic. Preferred aryl are monosubstituted or unsubstituted. If substituted, preferred substituents are selected from halo, amino, hydroxy, alkoxy, nitro, thio, oxo and trifluoromethyl, especially amino. Preferred aryl groups include, but are not limited to, phenyl, naphthyl, cyclopentadienyl, anthracyl, pyrene, pyridine, pyrimidine.

The term "arylalkyl" as used herein, unless otherwise indicated, means alkyl substituted with aryl.

The term "alkaryl" as used herein, unless otherwise indicated, means aryl substituted with alkyl.

DETAILED DESCRIPTION OF THE INVENTION

According to the present invention there is provided a hair care composition comprising at least one tyrosine compound and at least one other amino acid compound selected from tryptophan compounds, histidine compounds and lysine compounds. Preferably the compositions of the present invention a tyrosine compound and at least two other amino acid compounds selected from tryptophan compounds, histidine compounds and lysine compounds. More preferably the compositions of the present invention comprise at least one tyrosine compound, at least one tryptophan compound, at least one histidine compound and at least one lysine compound.

Preferably the amino acid compounds of the present invention have a water solubility of at least about 0.1 g/l, more preferably at least about 0.4 g/l, even more preferably at least about 1.0 g/l, at 25° C.

It is preferred that the tyrosine compounds comprise from about 0.001% to about 20%, more preferably from about 0.005% to about 5%, even more preferably from about 0.01% to about 1%, by weight, of total composition.

If present, it is preferred that the histidine compounds comprise from about 0.001% to about 20%, more preferably from about 0.005% to about 5%, even more preferably from about 0.01% to about 1%, by weight, of total composition.

If present, it is preferred that the lysine compounds comprise from about 0.001% to about 20%, more preferably from about 0.005% to about 5%, even more preferably from about 0.01% to about 1%, by weight, of total composition.

If present, it is preferred that the tryptophan compounds comprise from about 0.001% to about 20%, more preferably from about 0.005% to about 5%, even more preferably from about 0.01% to about 1%, by weight, of total composition.

Preferably the compositions of the present invention comprise from about 0.001% to about 20%, more preferably from about 0.01% to about 5%, even more preferably from about 0.1% to about 1.0%, by weight, of total amino acid compounds.

If the amino acid compounds herein contain a chiral centre then either stereoisomer is acceptable for use in the present compositions. However, preferred for use herein are amino acid derivatives in the L-form.

The amino acid compounds may be present in the compositions of the present invention either as discrete molecules or combined with other amino acid compounds to form a peptide. However, it is preferred that the amino acid compounds of the present invention are present as discrete molecules.

As used herein "tyrosine compounds" means compounds according to general formula (I):

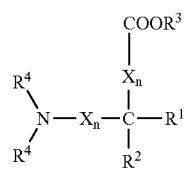

(I)

wherein;
each X is independently selected from substituted or unsubstituted, saturated or unsaturated carbon, preferably unsubstituted and saturated carbon;
n is 0-10, preferably 0-2, more preferably 0;
$R^1$ is selected from hydrogen, alkyl, arylalkyl or alkaryl, preferably hydrogen or alkyl, preferably hydrogen;
$R^2$ is selected from:

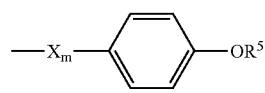

m is 0-6, preferably 0-2, more preferably 1;
$R^3$ is selected from hydrogen, alkyl, aryl, alkaryl, arylalkyl, and —$CF_3$, preferably hydrogen and alkyl, more preferably hydrogen and $C_1$-$C_4$ alkyl, even more preferably $C_1$-$C_2$ alkyl;
each $R^4$ is, independently, selected from hydrogen and alkyl, preferably hydrogen;
each $R^5$ is, independently, selected from hydrogen and alkyl, preferably hydrogen and methyl, more preferably hydrogen.

Preferred tyrosine compounds for use herein include tyrosine and ester derivatives of tyrosine compounds. More preferred are ester derivatives of tyrosine. Even more preferred are alkyl or aryl ester derivatives of tyrosine. More preferred still are alkyl, preferably $C_1$-$C_4$ alkyl, more preferably $C_1$-$C_2$ alkyl, more preferably $C_1$, alkyl ester derivatives of tyrosine.

Therefore, the compositions of the present invention preferably comprise at least one ester derivatives of tyrosine compounds and at least one other amino acid compound selected from tryptophan compounds, histidine compounds and lysine compounds.

As used herein "tryptophan compounds" means compounds according to general formula (I) wherein;
each X is independently selected from substituted or unsubstituted, saturated or unsaturated carbon, preferably unsubstituted and saturated carbon;
n is 0-10, preferably 0-2, more preferably 0;
$R^1$ is selected from hydrogen, alkyl, arylalkyl or alkaryl, preferably hydrogen or alkyl, preferably hydrogen;
$R^2$ is selected from:

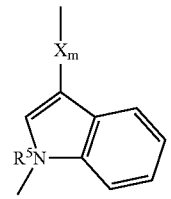

m is 0-6, preferably 0-2, more preferably 1;
$R^3$ is selected from hydrogen, alkyl, aryl, alkaryl, arylalkyl, and —$CF_3$, preferably hydrogen and alkyl, more preferably hydrogen and $C_1$-$C_4$ alkyl, even more preferably $C_1$-$C_2$ alkyl;
each $R^4$ is, independently, selected from hydrogen and alkyl, preferably hydrogen;
each $R^5$ is, independently, selected from hydrogen and alkyl, preferably hydrogen and methyl, more preferably hydrogen.

Preferred tryptophan compounds for use herein include tryptophan and ester derivatives of tryptophan. More preferred are ester derivatives of tryptophan. Even more preferred are alkyl or aryl ester derivatives of tryptophan. More preferred still are alkyl, preferably $C_1$-$C_4$ alkyl, more preferably $C_1$-$C_2$ alkyl, more preferably $C_1$, alkyl ester derivatives of tryptophan.

Therefore, the compositions of the present invention preferably comprise at least one tyrosine compound and at least one other amino acid compound selected from ester derivatives of tryptophan, histidine compounds and lysine compounds.

As used herein "histidine compounds" means compounds according to general formula (I) wherein;
each X is independently selected from substituted or unsubstituted, saturated or unsaturated carbon, preferably unsubstituted and saturated carbon;
n is 0-10, preferably 0-2, more preferably 0;
$R^1$ is selected from hydrogen, alkyl, arylalkyl or alkaryl, preferably hydrogen or alkyl, preferably hydrogen;

R² is selected from:

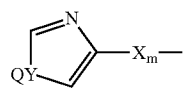

m is 0-6, preferably 0-2, more preferably 1;
Y is a heteroatom;
Q is selected from nil, hydrogen, aryl and alkyl, preferably hydrogen;
R³ is selected from hydrogen, alkyl, aryl, alkaryl, arylalkyl, and —CF₃, preferably hydrogen and alkyl, more preferably hydrogen;
each R⁴ is, independently, selected from hydrogen and alkyl, preferably hydrogen;

Preferred histidine compounds for use herein include histidine and ester derivatives of histidine. More preferred is histidine.

Therefore, the compositions of the present invention preferably comprise at least one tyrosine compound and at least one other amino acid compound selected from tryptophan compounds, histidine and lysine compounds.

As used herein "lysine compounds" means compounds according to general formula (I) wherein;
each X is independently selected from substituted or unsubstituted, saturated or unsaturated carbon, preferably unsubstituted and saturated carbon;
n is 0-10, preferably 0-2, more preferably 0;
R¹ is selected from hydrogen, alkyl, arylalkyl or alkaryl, preferably hydrogen or alkyl, preferably hydrogen;
R² is selected from —X$_b$—N(R⁵)₂;
b is 1-10, preferably 2-6, more preferably 4.
R³ is selected from hydrogen, alkyl, aryl, alkaryl, arylalkyl, and —CF₃, preferably hydrogen and alkyl, more preferably hydrogen;
each R⁴ is, independently, selected from hydrogen and alkyl, preferably hydrogen;
each R⁵ is, independently, selected from hydrogen and alkyl, preferably hydrogen and methyl, more preferably hydrogen.

Preferred lysine compounds for use herein include lysine and ester derivatives of lysine. More preferred is lysine. Therefore, the compositions of the present invention preferably comprise at least one tyrosine compound and at least one other amino acid compound selected from tryptophan compounds, histidine compounds and lysine.

Preferably the compositions of the present invention comprise at least one tyrosine compound and at least one, preferably two, more preferably three other amino acid compounds selected from ester derivatives of tryptophan, histidine and lysine.

More preferably the compositions of the present invention comprise at least one ester derivative of tyrosine compounds and at least one, preferably two, more preferably three amino acid compounds selected from ester derivatives of tryptophan, histidine and lysine.

A person skilled in the art could manufacture the amino acid compounds of the present invention using standard techniques. See, for example, *Organic Chemistry, Fifth Edition*, T. W. Graham Solomons, John Wiley & Sons Inc. (1992), pp 1092-1136.

Cosmetically Acceptable Carrier

The compositions of the present invention preferably comprise a cosmetically acceptable carrier. The phrase "cosmetically acceptable carrier", as used herein, means one or more compatible solid or liquid fillers, diluents, extenders and the like, which are cosmetically acceptable as defined hereinbelow. As used herein "cosmetically acceptable" means a material (e.g., compound or composition) which is suitable for use in contact with skin, hair or other suitable substrate as defined hereinbelow. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired. The compositions useful in the present invention may be a wide variety of product types. These include, but are not limited to, lotions, creams, gels, sticks, sprays, ointments, pastes, mousses, oils, waxes and suspensions. These product types may comprise several types of carriers including, but not limited to, solutions, aerosols, emulsions (including oil-in-water or water-in-oil), gels, solids, and liposomes.

Generally the compositions herein will comprise from about 50% to about 99.999%, preferably from about 90% to about 99.99%, more preferably from about 99% to about 99.9%, by weight, of carrier.

The carrier for use in the present compositions can comprise any suitable ingredient or combination of ingredients. However, preferably, the carrier for use in the present compositions will be suitable for use on hair. More preferably the carrier for use in the present compositions will be suitable for cleansing, conditioning, styling, treatment and/or care of hair. Even more preferably the carrier for use in the present compositions will comprise one or more hair conditioning agents.

Optional Ingredients

The compositions herein can contain a variety of optional components suitable for rendering the present compositions more cosmetically or aesthetically acceptable or to provide them with additional usage benefits. Such conventional optional ingredients are well-known to those skilled in the art. These include any cosmetically acceptable ingredients such as those found in the *CTFA International Cosmetic Ingredient Dictionary and Handbook, 7th edition*, edited by Wenninger and McEwen, (The Cosmetic, Toiletry, and Fragrance Association, Inc., Washington, D.C., 1997). Some non-limiting examples of these optional ingredients are given below.

Other Amino Acids/Peptides

The compositions of the present invention may optionally comprise other amino acid compounds and/or peptides, preferably at a level of from about 0.001% to about 20%, more preferably from about 0.01% to about 5%, by weight of total composition. If the present compositions comprise peptides it is preferred that said peptides contain from about 2 to about 10 amino acid residues. Preferred amino acid compounds for use herein, but are not limited to, cystine, cystine methyl ester, cystine dimethyl ester, cysteine, cysteine methyl ester, methionine methyl ester, methionine, alanine, glutamic acid, glutamic acid methyl ester, leucine, leucine methyl ester, serine, arginine, glutamine, threonine, asparagine, glycine, aspartic acid, aspartic acid methyl ester, phenylalanine, phenylalanine methyl ester, isoleucine, proline, valine and mixtures thereof. More preferred amino acid compounds for use herein are cystine, cystine methyl ester, cystine dimethyl ester, cysteine, cysteine methyl ester, methionine, methionine methyl ester, leucine, serine, arginine, phenylalanine, isoleucine, valine and mixtures thereof. Even more preferred amino acid compounds for use herein are cystine, cystine methyl ester, cystine dimethyl ester, methionine methyl ester, arginine, phenylalanine and mixtures thereof.

Conditioning Agent

The compositions herein may comprise one or more conditioning agents preferably in a level of from about 0.01% to about 25%, preferably from about 0.05% to about 10%, more preferably from about 0.1% to about 5%, by weight of total composition. Any cosmetically acceptable conditioning agent may be used in the compositions of the present invention. However, preferred conditioning agents for use in the present compositions include, but are not limited to, silicone conditioning agents and cationic conditioning agents.

Silicone Conditioning Component

The compositions of the present invention may optionally include a silicone conditioning component. The silicone conditioning component can comprise any suitable silicone conditioning agent but will generally comprise a silicone fluid conditioning agent. and can also comprise other ingredients, such as a silicone resin to enhance silicone fluid deposition efficiency or enhance glossiness of the hair (especially when high refractive index (e.g. above about 1.46 silicone conditioning agents are used (e.g. highly phenylated silicones)). Preferably the silicone is non-volatile, however volatile silicones are not excluded from use herein.

As used herein, "nonvolatile" refers to silicone material with little or no significant vapour pressure under ambient conditions, as is understood by those in the art. Boiling point under one atmosphere (atm) will preferably be at least about 250° C., more preferably at least about 275° C., most preferably at least about 300° C. Vapour pressure is preferably about 0.2 mm Hg at 25° C. or less, preferably about 0.1 mm Hg at 25° C. or less.

The silicone conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone conditioning agents for use in the compositions of the present invention will preferably have a viscosity of from about 20 to about 2,000,000 centistokes, more preferably from about 1,000 to about 1,800,000 centistokes, even more preferably from about 10,000 to about 1,500,000 centistokes, most preferably from about 30,000 to about 1,000,000 centistokes, at 25° C. The viscosity can be measured by means of a glass capillary viscometer as set forth in Dow Corning Corporate Test Method CTM0004, Jul. 20, 1970.

Silicone fluid for use in the present compositions include silicone oils which are flowable silicone materials with a viscosity of less than 1,000,000 centistokes, preferably between about 5 and 1,000,000 centistokes, more preferably between about 10 and about 600,000 centistokes, more preferably between about 10 and about 500,000 centistokes, most preferably between 10 and 350,000 centistokes at 25° C. Suitable silicone oils include, but are not limited to, polyalkyl siloxanes, polyaryl siloxanes, polyalkylaryl siloxanes, polyether siloxane copolymers, and mixtures thereof. Other insoluble, nonvolatile silicone fluids having conditioning properties can also be used.

Silicone oils for use in the composition include polyalkyl or polyaryl siloxanes which conform to following formula:

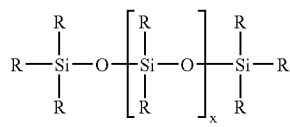

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the herein described compositions, are chemically stable under normal use and storage conditions, are insoluble in the compositions of the present invention, and are capable of being deposited on, and of conditioning, the hair.

The two R groups on the silicon atom of each monomeric silicone unit may represent the same group or different groups. Preferably, the two R groups represent the same group.

Preferred alkyl and alkenyl substituents are $C_1$-$C_5$ alkyls and alkenyls, more preferably from $C_1$-$C_4$, most preferably from $C_1$-$C_2$. The aliphatic portions of other alkyl alkenyl or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono di- and trialkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$-$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. For insoluble silicones the ethylene oxide and polypropylene oxide level must be sufficiently low to prevent solubility in water and the composition hereof.

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

References disclosing examples of some suitable silicone fluids for use in the present compositions include U.S. Pat. No. 2,826,551, U.S. Pat. No. 3,964,500, U.S. Pat. No. 4,364,837, British Patent 849,433, and Silicon Compounds, Petrarch Systems, Inc. (1984).

The silicone conditioning agent suitable for use in the present compositions can comprise silicone resins. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl dimethyl trimethyl monophenyl diphenyl methylphenyl monovinyl and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp. 204-308, John Wiley & Sons, Inc., 1989.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1. Insofar as the silicone resin forms a part of the same phase in the compositions hereof as the silicone fluid, i.e. the conditioning active, the sum of the fluid and resin should be included in determining the level of silicone conditioning agent in the composition.

The number average particle size of the optional silicone component can vary widely without limitation and will depend on the formulation and/or the desired characteristics. Number average particle sizes preferred for use in the present invention will typically range from about 10 nanometers to about 100 microns, more preferably from about 30 nanometers to about 20 microns.

Cationic Conditioning Component

The compositions of the present invention may optionally comprise a cationic conditioning component. The cationic conditioning component may comprise any suitable cationic conditioning agent or mixtures of cationic conditioning agents.

Preferred cationic conditioning agents for use herein include, but are not limited to, polymeric cationic conditioning agents. Preferably the cationic polymer conditioning agent will preferably be water soluble. The total level of cationic polymers in the compositions of the present invention is typically from about 0.001% to about 20%, more typically from about 0.005% to about 10%, preferably from about 0.01% to about 2%, by weight.

By "water soluble" cationic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

As used herein, the term "polymer" shall include materials whether made by polymerisation of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density will be preferably at least about 0.1 meq/g, more preferably at least about 0.5 meq/g, even more preferably at least about 1.1 meq/g, most preferably at least about 1.2 meq/g. Generally, for practical purposes, the cationic polymers will have a cationic charge density of less than about 7 meq/g, preferably less than about 5 meq/g, more preferably less than about 3.5 meq/g, even more preferably less than about 2.5 meq/g. Cationic charge density of the cationic polymer can be determined using the Kjeldahl Method (United States Pharmacopoeia—Chemical tests—<461> Nitrogen Determination—method II). Those skilled in the art will recognise that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the *CTFA International Cosmetic Ingredient Dictionary and Handbook, 7th edition*, edited by Wenninger and McEwen, (The Cosmetic, Toiletry, and Fragrance Association, Inc., Washington, D.C., 1997).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$-$C_7$ alkyl groups, more preferably $C_1$-$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerised in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$-$C_7$ alkyl, more preferably a $C_1$-$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$-$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: polymeric quaternary ammonium salt of hydroxyethylcellulose (referred to in the industry by the Cosmetic, Toiletry, and Fragrance Association, "CTFA", as Polyquaternium-10), such as those commercially available from Amerchol under the tradename UCARE Polymer JR-30M; copolymers of hydroxyethylcellulose and diallyldimethyl ammonium chloride (referred to in the industry by the Cosmetic, Toiletry, and Fragrance Association, "CTFA", as Polyquaternium-4), such as those commercially available from National Starch under the tradename Celquat L-200 and Celquat H-100; copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g. sodium polystyrene sulfonate).

Other suitable conditioning agents for use herein include, but are not limited to, quaternary ammonium conditioning agents, such as ester substituted quaternary ammonium compounds, amide substituted quaternary ammonium compounds and alkyl substituted quaternary ammonium compounds such as cetyl trimethyl ammonium chloride and those quaternary ammonium compounds disclosed in U.S. Pat. No. 5,610,187 (Witco), mixed amide/ester substituted quaternary ammonium compounds such as those disclosed in EP-A-682935 (Kao) and protonated amines. Another suitable conditioning agent for use herein is a protonated amine, derived from amines having the formula $NR_3$ wherein each R is independently selected from $C_1$-$C_4$ alkyl or $C_8$-$C_{22}$ alkyl, provided that at least one of the R groups is $C_8$-$C_{22}$ alkyl.

A commercially available diester quaternary ammonium compound for use herein has the tradename Tetranyl Co-40 and is supplied by Kao. The INCI name for this material is Dioleylethyl Hydroxyethylmonium methosulfate.

Surfactants

The compositions of the present invention can comprise a surfactant or mixture of surfactants. If present, the surfactant system will preferably be present in the compositions herein at an active level of from about 0.001% to about 30%, more preferably from about 0.01% to about 25%, even more preferably from about 0.1% to about 20%. It should be recognised, however, that the concentration of the surfactant system may vary with the purpose the surfactants are intended to serve, the cleaning or lather performance desired, the surfactants incorporated into the surfactant system, the desired product concentration, the presence of other components in the composition, and other factors well known in the art.

Surfactant systems useful herein can comprise one or more surfactants selected from anionic surfactants, amphoteric surfactants, nonionic surfactants, cationic surfactants and mixtures thereof.

Amphoteric surfactant components useful in the present composition include those known to be useful in personal cleansing compositions, and which, preferably, contain a group that is anionic at the pH of the compositions of the present invention. The active concentration of such surfactant components in the surfactant system of the present invention preferably ranges from about 0.001% to about 20%, more preferably from about 0.01% to about 15%, and most preferably from about 0.1% to about 10% by weight of the surfactant system. Examples of amphoteric surfactants suitable for use in the composition herein are described in U.S. Pat. No. 5,104,646 (Bolich Jr. et al.) and U.S. Pat. No. 5,106,609 (Bolich Jr. et al.). Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauroamphoacetate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL™" and described in U.S. Pat. No. 2,528,378.

Other amphoterics, sometimes classified as zwitterionics, such as betaines can also be used in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

Anionic surfactants suitable for use in the present invention include alkyl sulfate, alkyl ethoxylated sulfate, or a mixture thereof. These materials have the respective formulae (I) $ROSO_3M$ and (II) $RO(C_2H_4O)_x SO_3M$, wherein R is alkyl or alkenyl of from about 8 to about 30 carbon atoms, x is 1 to 10, and M is H or a salt-forming cation such as ammonium, alkanolamine containing $C_1$-$C_3$ alkyl groups such as triethanolamine, and monovalent and polyvalent metals such as the alkaline and alkaline earth metals. Preferred metals include sodium, potassium, magnesium, and calcium. The cation M, of the anionic surfactant should preferably be chosen such that the anionic surfactant component is water soluble. Solubility of anionic surfactants, in general, will depend upon the particular anionic surfactants and cations chosen. As an aid to determining appropriate mixtures of anionic surfactants, the anionic surfactants should be chosen such that the Krafft temperature is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralised.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. The sulfate surfactant is preferably comprised of a combination of ethoxylated and nonethoxylated sulfates. Alkyl sulfates can provide excellent cleaning and lather performance. Alkyl ethoxylated sulfates can provide excellent cleaning performance.

Other suitable anionic detersive surfactants include, but are not limited to water-soluble salts of organic, sulfuric acid reaction products of the general formula [$R_1$—$SO_3$—M] where $R_1$ is selected from the group consisting of a straight or branched chain, saturated aliphatic hydrocarbon radical having from about 8 to about 24, preferably about 10 to about 18, carbon atoms; and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen. Examples of such detersive surfactants are the salts of an organic sulfuric acid reaction product of a hydrocarbon of the methane series, including iso neo and n-paraffins, having about 8 to about 24 carbon atoms, preferably about 10 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $Cl_{10-18}$ n-paraffins.

Another class of anionic detersive surfactants suitable for use in the present invention are the reaction products of fatty acids esterified with isethionic acid and neutralised with sodium hydroxide where, for example, the fatty acids are derived from coconut oil or palm kernal oil; sodium, ammonium, tetraethylammonium or potassium salts of fatty acid amides of methyl tauride in which the fatty acids, for example, are derived from coconut oil or palm kernal oil. Other similar anionic surfactants are described in U.S. Pat. No. 2,486,921; U.S. Pat. No. 2,486,922; and U.S. Pat. No. 2,396,278.

Other anionic detersive surfactants suitable for use in the present invention are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic detersive surfactants include alkyl glyceryl ether sulfonate surfactants (also referred to herein as an "AGS" surfactant), derivatives thereof and salts thereof. These AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

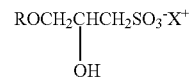 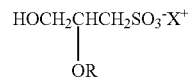

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof. More preferably, the alkyl radicals, R in the above formulas, are saturated and straight chain.

Without being limited by theory, it is believed that the distribution of alkyl chain lengths in the AGS surfactant has some effect on the character of the overall cleansing composition. A satisfactory distribution can be achieved in a commercially practicable way by using fatty alcohols derived from coconut oil and tallow. An equivalent distribution of alkyl chain lengths can be achieved using other starting materials. In the preparation of the coconut fatty alcohols used to provide the alkyl group of the AGS, preferably the middle cut of the coconut oil is taken. The higher boiling cut can be retained with the middle cut coconut oils if desired. In the preparation of the tallow fatty alcohols, a hydrogenation step is included to insure that they are substantially saturated.

Preferred AGS compounds are those where the alkyl group is derived from at least about 50% from alcohols of about 10 to about 18 carbons, having mainly monoglyceryl radicals present, with less than about 30% of diglyceryl radicals present. The term "AGS" is intended to include monoglyceryl, diglyceryl, and traces of the higher glyceryl compounds. Small amounts, that is less than about 3% total, of triglyceryl ether sulfonates and tetraglyceryl ether sulfonates can be present. Also included are AGS's derived from glyceryl ethers having branched or mixed branched and straight chain lengths that emulate the straight chain lengths.

The AGS surfactants useful in the present invention are more fully described in U.S. Pat. No. 2,979,465, to Parran et al., issued Apr. 11, 1961; U.S. Pat. No. 3,179,599, to Eaton et al., issued Apr. 20, 1965; British Patent No. 848,224, published Sep. 14, 1960; British Patent No. 791,415, published Mar. 5, 1958; U.S. Pat. No. 5,322,643, to Schwartz et al., issued Jun. 21, 1994; and U.S. Pat. No. 5,084,212, to Farris et al. issued Jan. 28, 1992. These references also disclose various cleansing products in which the AGS surfactant of this invention can be used.

Still other suitable anionic detersive surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 10 to about 24 carbon atoms, preferably about 12 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880.

Another class of anionic detersive surfactants suitable for use in the present invention are the beta-alkyloxy alkane sulfonates. These compounds have the following formula:

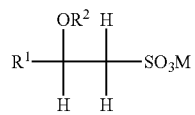

where $R^1$ is a straight chain alkyl group having from about 6 to about 20 carbon atoms, $R^2$ is a lower alkyl group preferably having from about 1 to about 3 carbon atoms, and M is a water-soluble cation as described hereinabove.

Preferred additional anionic detersive surfactants for use in the compositions of the present invention include, but are not limited to, alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

If present, the anionic detersive surfactants are preferably present in the surfactant system of the present invention at total active concentration level of from about 3% to about 30%, preferably from about 4% to about 20%, most preferably from about 6% to about 17%.

Another class of anionic surfactants is fatty acid soaps. Though useful to the present invention, high concentrations of these surfactants in the presence of hard water tend to result in significant build-up on the hair and skin, adversely affecting cleansing and hair and skin feel. Accordingly, if added to the compositions of the present invention, the level of the fatty acid soaps is preferably incorporated at concentration levels of less than about 3%, more preferably less than about 1%.

Surfactant systems useful in the present invention may also include nonionic surfactants, cationic surfactants, and combinations thereof. Suitable classes of nonionic surfactants include, but are not limited to:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerised propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

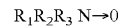

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Non-limiting examples of amine oxides suitable for use in this invention include dimethyl-dodecylamine oxide, oleyidi(2-hydroxyethyl) amine oxide, dimethyloctylamine oxide, dimethyl-decylamine oxide, dimethyl-tetradecylamine oxide, 3,6,9-tri-oxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides include, but are not limited to: dodecyldimethylphosphine oxide, tetradecyidimethylphosphine oxide, tetradecylmethylethylphosphine oxide, 3,6,9,-trioxaoctadecyidimethylphosphine oxide, cetyidimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyidipropylphosphine oxide, dodecyidi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyidimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include, but are not limited to: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polyalkylene oxide modified dimethylpolysiloxanes, also known as dimethicone copolyols. These materials include the polyalkylene oxide modified dimethylpolysiloxanes of the following formulae:

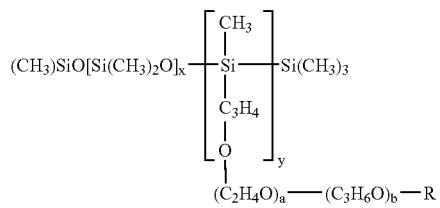

and

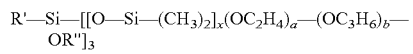

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30. Dimethicone copolyols among those useful herein are disclosed in the following patent documents: U.S. Pat. No. 4,122,029, Gee et al., issued Oct. 24, 1978; U.S. Pat. No. 4,265,878, Keil, issued May 5, 1981; and U.S. Pat. No. 4,421,769, Dixon et al., issued Dec. 20, 1983. Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.).

Surfactant systems useful in the present invention may also comprise cationic surfactants. Cationic surfactants typically contain amino or quaternary ammonium hydrophilic moieties which are positively charged when dissolved in the aqueous composition of the present invention. Cationic surfactants among those useful herein are disclosed in the following documents: M. C. Publishing Co., McCutcheon's, *Detergents & Emulsifiers*, (*North American edition* 1989); Schwartz, et al., *Surface Active Agents, Their Chemistry and Technology*. New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

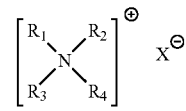

wherein $R_1$—$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

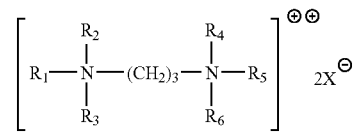

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include monoalkyltrimethylammonium chlorides and dialkyldimethylammonium chlorides and trialkyl methyl ammonium chlorides, wherein at least one of the alkyl groups have from about 12 to about 22 carbon atoms and are derived from long-chain fatty acids, such as hydrogenated tallow fatty acid (tallow fatty acids yield quaternary compounds wherein the long chain alkyl groups are predominately from 16 to 18 carbon atoms). Examples of quaternary ammonium salts useful in the present invention include, but are not limited to, stearyl trimethyl ammonium chloride, ditallowedimethyl ammonium chloride, ditallowedimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(cocnutalkyl) dimethyl ammonium chloride, and stearyl dimethyl benzyl ammonium chloride, ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride and tricetyl methyl ammonium chloride are particularly preferred quaternary ammonium salts.

Other surfactants may be used in the surfactant system of the present invention, that the surfactant is also chemically and physically compatible with the essential components of the present invention, or does not otherwise unduly impair product performance, aesthetics or stability.

Sensates

The compositions of the present invention may also comprise a sensate. As used herein the term "sensate" means a substance that, when applied to the skin, causes a perceived sensation of a change in conditions, for example, but not limited to, heating, cooling, refreshing and the like.

Sensates are preferably utilized at levels of from about 0.001% to about 10%, more preferably from about 0.005% to about 5%, even more preferably from about 0.01% to about 1%, by weight, of the total composition.

Any sensate suitable for use in hair care compositions may be used herein. A non-limiting, exemplary list of suitable sensates can be found in GB-B-1315626, GB-B-1404596 and GB-B-1411785. Preferred sensates for use in the compositions herein are camphor, menthol, I-isopulegol, ethyl menthane carboxamide and trimethyl isopropyl butanamide.

$C_1$-$C_6$ Aliphatic Alcohols

The compositions of the present invention may optionally comprise $C_1$-$C_6$, preferably $C_2$-$C_3$, more preferably $C_2$, aliphatic alcohol. The aliphatic alcohol will generally comprise from about 1% to about 75%, preferably from about 10% to about 40%, more preferably from about 15% to about 30%, even more preferably from about 18% to about 26%, by weight, of the total composition.

Viscosity Modifier

The compositions of the present invention can also comprise viscosity modifiers. Any viscosity modifier suitable for use in hair care compositions may be used herein. Generally, if present, the viscosity modifier will comprise from about 0.01% to about 10%, preferably from about 0.05% to about 5%, more preferably from about 0.1% to about 3%, by weight, of the total composition. A non-limiting list of suitable viscosity modifiers can be found in the *CTFA International Cosmetic Ingredient Dictionary and Handbook, 7th edition*, edited by Wenninger and McEwen, (The Cosmetic, Toiletry, and Fragrance Association, Inc., Washington, D.C., 1997).

Suitable viscosity modifiers for use herein include shear sensitive viscosity modifiers. As used herein "shear sensitive viscosity modifiers" means viscosity modifiers that can form compositions whose viscosity decreases at low shear rates. Shear rate ($s^{-1}$) can be defined as the ratio of the velocity ($ms^{-1}$) of material to its distance from a stationary object (m). Shear rates of less than about $250s^{-1}$ can be thought of as "low shear rates". Any shear sensitive viscosity modifier suitable for use in hair care may be used herein However, preferred for use herein are viscosity modifiers which form compositions whose viscosity decreases at a shear rate of less than about $100s^{-1}$ more preferably less than about $50s^{-1}$. In addition, preferred shear sensitive viscosity modifiers are those which can form compositions whose viscosity decreases by more than about 30%, preferably more than about 50%, more preferably more than about 70%, even more preferably more than about 80% at a shear rate of $50s^{-1}$.

Preferred viscosity modifiers for use herein are those which form compositions whose viscosity is also sensitive to the electrolyte concentration in the aqueous phase, known hereafter as "salt sensitive viscosity modifiers". Background material on the properties of salt sensitive viscosity modifiers can be found in *American Chemical Society Symposium Series* (1991), Vol. 462, pp 101-120. Any salt sensitive viscosity modifier suitable for use in hair care compositions may be used herein.

Examples of suitable viscosity modifiers include, but are not limited to, synthetic hectorites, carboxylic anionic polymers/copolymers and carboxylic anionic cross-linked polymers/copolymers. Preferred for use herein are carboxylic anionic cross-linked polymers and copolymers. More preferred are carboxylic anionic cross-linked copolymers.

The synthetic hectorites useful herein are synthetic layered silicates such as sodium-magnesium silicate. Examples of suitable synthetic hectorites include those available from Laporte Plc., United Kingdom under the trade name Laponite.

The carboxylic anionic copolymers useful herein can be hydrophobically-modified cross-linked copolymers of carboxylic acid and alkyl carboxylate, and have an amphiphilic property. These carboxylic anionic copolymers are obtained by copolymerising 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

$$R^1-\underset{\underset{CH_2}{\|}}{C}-Y^1-Y^2-Y^1-\underset{\underset{CH_2}{\|}}{C}-R^1$$

wherein $R^1$ is a hydrogen or an alkyl group having from about 1 to about 30 carbons; $Y^1$, independently, is oxygen, $CH_2O$, COO, OCO,

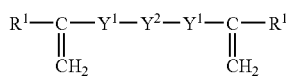, or 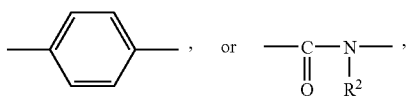, wherein $R^2$ is a hydrogen or an alkyl group having from about 1 to about 30 carbons; and $Y^2$ is selected from $(CH_2)_{m''}$, $(CH_2CH_2O)_{m''}$, or $(CH_2CH_2CH_2O)$ m" wherein m" is an integer of from 1 to about 30.

Suitable carboxylic anionic copolymers herein are acrylic acid/alkyl acrylate copolymers having the following formula:

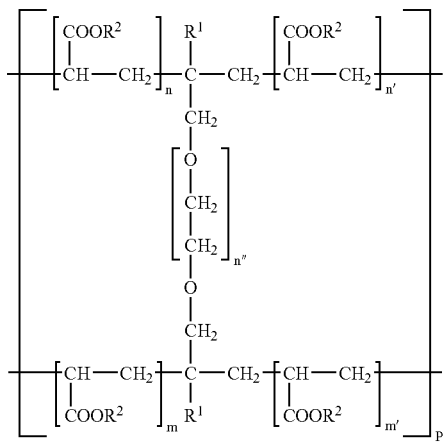

wherein $R^2$, independently, is a hydrogen or an alkyl of 1 to 30 carbons wherein at least one of $R^2$ is a hydrogen, $R^1$ is as defined above, n, n', m and m' are integers in which n+n'+m+m' is from about 40 to about 100, n" is an integer of from 1 to about 30, and P is defined so that the copolymer has a molecular weight of about 5000 to about 3,000,000.

Neutralizing agents may be included to neutralize the carboxylic anionic copolymers herein. Non-limiting examples of such neutralizing agents include sodium hydroxide, potassium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Non-limiting examples of suitable carboxylic anionic viscosity modifiers, including details of their manufacture, can be found in U.S. Pat. Nos. 3,940,351; 5,288,814; 5,349,030; 5,373,044 and 5,468,797. Examples of carboxylic anionic viscosity modifiers include those available from B.F. Goodrich, Cleveland, Ohio, USA under the trade names Pemulen TR-1, Pemulen TR-2, Carbopol 980, Carbopol 981, Carbopol ETD-2020, Carbopol ETD-2050 and Carbopol Ultrez 10. Preferred are Carbopol ETD-2020, Carbopol ETD-2050 and Carbopol Ultrez 10, especially Carbopol Ultrez 10.

Particularly preferred viscosity modifiers for use herein from the viewpoint of improving spreadability, reducing tack and improving shine are carboxylic anionic viscosity modifiers such as Carbopol Ultrez 10.

Polyethylene Glycol Derivatives of Glycerides

Suitable polyethylene glycol derivatives of glycerides include any polyethylene glycol derivative of glycerides which are water-soluble and which are suitable for use in a hair care composition. Suitable polyethylene glycol derivatives of glycerides for use herein include derivatives of mono di- and tri-glycerides and mixtures thereof.

One class of polyethylene glycol derivatives of glycerides suitable herein are those which conform to the general formula (I):

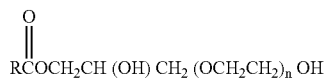

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms.

Suitable polyethylene glycol derivatives of glycerides can be polyethylene glycol derivatives of hydrogenated castor oil. For example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Preferred for use in the compositions herein is PEG-60 hydrogenated castor oil.

Other suitable polyethylene glycol derivatives of glycerides can be polyethylene glycol derivatives of stearic acid. For example, PEG-30 stearate, PEG-40 stearate, PEG-50 stearate, PEG-75 stearate, PEG-90 stearate, PEG-100 stearate, PEG-120 stearate, and PEG-150 stearate. Preferred for use in the compositions herein is PEG-100 stearate.

Fatty Alcohols

The compositions of the present invention may also comprise fatty alcohols. Any fatty alcohol suitable for use in hair care may be used herein. However, preferred are $C_8$ to $C_{22}$, more preferred are $C_{12}$ to $C_{18}$, even more preferred are $C_{16}$, fatty alcohols.

Fatty alcohols are preferably utilized at levels of from about 0.1% to about 20%, more preferably from about 0.25% to about 10%, most preferably from about 0.5% to about 5%, by weight of the composition.

If both fatty alcohol and cationic surfactant are present the ratio of alcohol:surfactant is preferably in the range of from about 3:1 to about 6:1, more preferably 4:1.

Water

The compositions of the present invention will also preferably comprise water. When present water will generally comprise from about 25% to about 99%, preferably from about 50% to about 98%, by weight, of the total composition.

A wide variety of additional ingredients can be formulated into the present composition. These include: other hair conditioning ingredients such as panthenol, pantethine, pantotheine, panthenyl ethyl ether, and combinations thereof; other solvents such as hexylene glycol; hair-hold polymers such as those described in WO-A-94/08557; viscosity modifiers and suspending agents such as xanthan gum, guar gum, hydroxyethyl cellulose, triethanolamine, methyl cellulose, starch and starch derivatives; viscosity modifiers such as methanolamides of long chain fatty acids such as cocomonoethanol amide; crystalline suspending agents; pearlescent aids such as ethylene glycol distearate; opacifiers such as polystyrene; preservatives such as phenoxyethanol, benzyl alcohol, methyl paraben, propyl paraben, imidazolidinyl urea and the hydantoins; polyvinyl alcohol; ethyl alcohol; pH adjusting agents, such as lactic acid, citric acid, sodium citrate, succinic acid, phosphoric acid, sodium hydroxide, sodium carbonate; salts, in general, such as potassium acetate and sodium chloride; colouring agents, such as any of the FD&C or D&C dyes; hair oxidising (bleaching) agents, such as hydrogen peroxide, perborate and persulfate salts; hair reducing agents, such as the thioglycolates; perfumes; sequestering agents, such as disodium ethylenediamine tetra-acetate; anti-dandruff agents such as anti-dandruff agents such as zinc pyrithione (ZPT), sulfur, selenium sulfide, coal tar, piroctone olamine, ketoconazole, climbazole, salicylic acid; antioxidants/ultra violet filtering agents such as octylmethoxycinnamate, benzophenone-3 and DL-alpha tocopherol acetate and polymer plasticizing agents, such as glycerine, diisobutyl adipate, butyl stearate, and propylene glycol. Such optional ingredients generally are used individually at levels from about 0.001% to about 10.0%, preferably from about 0.05% to about 5.0% by weight of the composition.

Product Forms

The hair care compositions of the present invention can be formulated in a wide variety of product forms, including but not limited to creams, gels, aerosol or non-aerosol foams, mousses and sprays. Mousses, foams and sprays can be formulated with propellants such as propane, butane, pentane, dimethylether, hydrofluorocarbon, $CO_2$, $N_2O$, nitrogen or without specifically added propellants (using air as the propellant in a pump spray or pump foamer package).

Method of Use

The compositions of the present invention may be used in a conventional manner for treating a suitable substrate. As used herein the term "suitable substrate" means any surface to which the present composition may be applied without an unduly adverse effect. Suitable substrates include, but are not limited to keratinous materials such as skin and hair. Preferably the present compositions are applied to hair, especially human hair.

An effective amount of the composition, typically from about 1 gram to about 50 grams, preferably from about 1 gram to about 20 grams, is applied to the substrate. The composition may be applied in any suitable manner including, but not limited to, spraying the composition on to the substrate, working the composition onto the substrate, generally with the hands and fingers or with a suitable implement such as a comb or brush.

EXAMPLES

The following examples further illustrate the preferred embodiments within the scope of the present invention. The examples are given solely for the purposes of illustration and are not to be construed as limitations of the present invention as many variations of the invention are possible without departing from its spirit or scope. Unless otherwise indicated, all ingredients are expressed on a weight percentage of the active ingredient.

Example I (Shampoo)

| | Wt % |
|---|---|
| Ammonium Laureth Sulfate (60%) | 25.0 |
| Lauramide DEA | 4.0 |
| Water | 69.7 |
| Lysine | 0.1 |
| Tyrosine methyl ester | 0.1 |
| Tryptophan methyl ester | 0.1 |
| Histidine | 0.1 |
| Methionine | 0.1 |
| Hydroxypropyl Methyl Cellulose | 0.6 |
| Methylchloroisothiazolinone and Methylisothiazolinone | 0.1 |
| Fragrance | 0.1 |

1. Mix water and hydroxypropyl methyl cellulose until completely dissolved.
2. Add ammonium laureth sulfate very slowly with slow agitation.
3. Add lauramide DEA very slowly with slow agitation, to avoid air entrapment.
4. Add methylchloroisothiazolinone/methylisothiazolinone.
5. Add lysine, tyrosine methyl ester, tryptophan methyl ester, histidine and methionine.
6. Add fragrance.

Example II (2-in-1 Shampoo)

| | Wt % |
|---|---|
| Ammonium Laureth Sulfate (60%) | 25.0 |
| Lauramide DEA | 4.0 |
| Water | 66.5 |
| Lysine | 0.1 |
| Cystine dimethyl ester | 0.4 |
| Tyrosine | 0.1 |
| Tryptophan Methyl Ester | 0.1 |
| Hydroxypropyl Methyl Cellulose | 0.6 |
| Methylchloroisothiazolinone and Methylisothiazolinone | 0.1 |
| Dimethicone Copolyol | 3.0 |
| Fragrance | 0.1 |

1. Mix water and hydroxypropyl methyl cellulose until completely dissolved.
2. Add ammonium laureth sulfate very slowly with slow agitation.
3. Add lauramide DEA very slowly with slow agitation, to avoid air entrapment.
4. Add dimethicone copolyol and methylchloroisothiazolinone/methylisothiazolinone.
5. Add lysine, cystine dimethyl ester, tyrosine and tryptophan methyl ester.
6. Add fragrance.

Example III (Conditioner)

| | Wt % |
|---|---|
| Part A | |
| Water | 91.4 |
| Quaternium-15 | 0.5 |
| Tyrosine methyl ester | 0.1 |
| Lysine | 0.1 |
| Histidine | 0.1 |
| Cystine dimethyl ester | 0.3 |
| Part B | |
| Cetyl alcohol | 3.5 |
| Stearamidopropyl dimethylamine | 1.0 |
| Part C | |
| Cyclomethicone | 3.0 |

1. Dissolve quaternium-15, histidine, lysine, tyrosine methyl ester and cystine dimethyl ester in water with moderate agitation. Heat to 65° C.
2. Melt together cetyl alcohol and stearamidopropyl dimethylamine. Add to part A.
3. Add cyclomethicone. Stir for 5 minutes.

Example IV (Hairspray)

|  | Wt % |
| --- | --- |
| Ethanol | 68.7 |
| Octylacrylamide/acrylates/butylaminoethyl methacrylate copolymer | 2.0 |
| Cyclomethicone | 0.8 |
| Aminomethyl propanol | 0.3 |
| Perfume | 0.3 |
| Cystine diethyl ester | 0.4 |
| Lysine ethyl ester | 0.2 |
| Histidine | 0.1 |
| Tyrosine | 0.1 |
| Methionine methyl ester | 0.1 |
| N-butane/propane/isobutane (BPAP48)[a] | 27.0 |

[a]available from BP, London, GB

1. Dissolve octylacrylamide/acrylates/butylaminoethyl methacrylate copolymer in ethanol with agitation.
2. Add cyclomethicone, aminomethyl propanol, methionine methyl ester, cystine diethyl ester, lysine ethyl ester, histidine, tyrosine and perfume.
3. Pack into aerosol can and gas product with N-butane/propane/isobutane.

Example V (Gel)

|  | Wt % |
| --- | --- |
| PVP K-90 | 2.9 |
| Sodium Hydroxide (10%) | 1.9 |
| Quaternium-15 | 0.1 |
| Water | 90.3 |
| Cystine dimethyl ester | 0.4 |
| Tyrosine methyl ester | 0.1 |
| Tryptophan ethyl ester | 0.1 |
| Lysine | 0.2 |
| Histidine | 0.1 |
| Methionine | 0.1 |
| Acrylates/Steareth-20 Itaconate Copolymer[a] | 3.8 |

[a]available from BASF, Ludwigshafen, DE

1. Add PVP K-90, sodium hydroxide, quaternium-15, cystine dimethyl ester, tyrosine methyl ester, tryptophan ethyl ester, lysine, histidine and methionine to the water with agitation.
2. Once fully dispersed, add acrylates/steareth-20 itaconate copolymer with moderate agitation.

Example VI (Conditioning Spray)

|  | Wt % |
| --- | --- |
| Water | 97.8 |
| Polyquaternium-4 | 0.3 |
| Benzyl alcohol | 0.5 |
| Methyl paraben | 0.2 |
| Fragrance | 0.2 |
| Isosteareth-20 | 0.3 |
| Panthenol | 0.1 |
| Lysine methyl ester | 0.2 |
| Methionine propyl ester | 0.1 |
| Tyrosine methyl ester | 0.1 |
| Histidine methyl ester | 0.2 |

1. Heat the water to 60° C. and add isosteareth-20. After 10 minutes, reduce temperature to 30° C.
2. Add polyquaternium-4, benzyl alcohol, methyl paraben, fragrance.
3. Add panthenol, lysine methyl ester, methionine propyl ester, tyrosine methyl ester and histidine methyl ester.

Example VII (Mousse)

|  | Wt % |
| --- | --- |
| Water | 87.6 |
| Polyquaternium-4 | 1.6 |
| Propylene glycol | 0.3 |
| DMDM Hydantoin | 0.2 |
| Cocamidopropyl betaine | 0.5 |
| Perfume | 0.2 |
| Cystine dimethyl ester | 0.3 |
| Tryptophan | 0.1 |
| Tyrosine | 0.1 |
| Lysine | 0.1 |
| N-butane/propane/isobutane (BPAP48) | 9.0 |

1. Add polyquaternium-4 to the water.
2. Add propylene glycol, DMDM hydantoin, perfume, tryptophan, cystine dimethyl ester, tyrosine, lysine and cocamidopropyl betaine.
3. Pack into aerosol can and gas product with N-butane/propane/isobutane.

Example VIII (Leave-in Cream)

|  | Wt % |
| --- | --- |
| Water | 81.7 |
| Ceteareth-25 | 1.9 |
| Cetyl alcohol | 2.8 |
| Stearyl alcohol | 2.8 |
| Ethanol | 10.0 |
| Fragrance | 0.3 |
| Tyrosine ethyl ester | 0.2 |
| Lysine | 0.3 |

1. Add ceteareth-25, cetyl alcohol and stearyl alcohol to water and heat to 80° C. with stirring.
2. Hold for 5 minutes before cooling.
3. Begin to apply high shear mixing. At 45° C., stop high shear mixing and add ethanol, fragrance, tyrosine ethyl ester and lysine with stirring.
4. Cool to room temperature.

Example IX (Colourant)

|  | Wt % |
|---|---|
| 2-Methyl-1-naphthol | 0.44 |
| p-aminophenol | 0.28 |
| Propylene glycol | 25.00 |
| Sodium sulfite | 0.20 |
| Ammonium hydroxide | qs pH9 |
| Tyrosine ethyl ester | 0.20 |
| Lysine | 0.15 |
| Histidine | 0.10 |
| Methionine methyl ester | 0.10 |
| Water | qs |

All the materials are combined with the water and the pH is adjusted to 9 with ammonium hydroxide. This should then added to half the amount of 20 vol % hydrogen peroxide solution prior to application to the hair.

The invention claimed is:

1. A hair care composition comprising:
a) at least one ester derivative of tyrosine;
b) at least one other amino acid compound selected from tryptophan compounds, histidine compounds and lysine compounds; and
c) a cosmetically acceptable carrier which is suitable for use on hair, said cosmetically acceptable carrier comprising one or more hair conditioning agents selected from the group consisting of silicone conditioning agents and cationic conditioning agents.

2. A hair care composition comprising:
a at least one ester derivative of tyrosine;
b) at least two other amino acid compound selected from tryptophan compounds, histidine compounds and lysine compounds; and
c) a cosmetically acceptable carrier which is suitable for use on hair, said cosmetically acceptable carrier comprising one or more hair conditioning agents selected from the group consisting of silicone conditioning agents and cationic conditioning agents.

3. A hair care composition comprising:
a) at least one ester derivative of tyrosine;
b) at least one histidine compound;
c) at least one lysine compound; and
d) a cosmetically acceptable carrier which is suitable for use on hair, said cosmetically acceptable carrier comprising one or more hair conditioning agents selected from the group consisting of silicone conditioning agents and cationic conditioning agents.

4. A composition according to claim 1 wherein said amino acid compounds have a water solubility of at least about 0.1 g/l at 25° C.

5. A composition according to claim 1 wherein said ester derivative of tyrosine is an alkyl or aryl ester derivative of tyrosine.

6. A composition according to claim 1 wherein said ester derivative of tyrosine is a $C_1$-$C_4$ alkyl ester derivative of tyrosine.

7. A cosmetic method of treating hair comprising applying a composition according to claim 1 to said hair.

* * * * *